United States Patent
Hsu et al.

(10) Patent No.: US 9,850,323 B2
(45) Date of Patent: Dec. 26, 2017

(54) HIGH CONCENTRATION CHITOSAN-NUCLEIC ACID POLYPLEX COMPOSITIONS

(71) Applicant: enGene, Inc., Vancouver (CA)

(72) Inventors: Eric Hsu, Vancouver (CA); Carlos Fleet, Vancouver (CA); Anthony Cheung, Vancouver (CA); Jun Gao, Coquitlam (CA)

(73) Assignee: ENGENE, INC., Montreal (CA)

( * ) Notice: Subject to any disclaimer, the term of this patent is extended or adjusted under 35 U.S.C. 154(b) by 0 days.

(21) Appl. No.: 14/266,584

(22) Filed: Apr. 30, 2014

(65) Prior Publication Data

US 2014/0350091 A1   Nov. 27, 2014

Related U.S. Application Data

(63) Continuation of application No. 12/680,527, filed as application No. PCT/CA2008/001714 on Sep. 26, 2008, now Pat. No. 8,722,646.

(60) Provisional application No. 60/976,316, filed on Sep. 28, 2007.

(51) Int. Cl.

| C08B 37/00 | (2006.01) |
| C07H 17/02 | (2006.01) |
| A61K 31/7088 | (2006.01) |
| C12N 15/87 | (2006.01) |

(52) U.S. Cl.
CPC ...... *C08B 37/0063* (2013.01); *A61K 31/7088* (2013.01); *C07H 17/02* (2013.01); *C12N 15/87* (2013.01); *Y10T 428/2982* (2015.01)

(58) Field of Classification Search
CPC ............................. A61K 31/7088; C12N 15/87
USPC ............................................ 514/44; 424/450
See application file for complete search history.

(56) References Cited

U.S. PATENT DOCUMENTS

| 6,184,037 B1 * | 2/2001 | Rolland et al. ............... 435/455 |
| 6,537,813 B1 * | 3/2003 | Chen et al. .................... 435/455 |

FOREIGN PATENT DOCUMENTS

| WO | WO 97/42975 A2 | 11/1997 |
| WO | WO 98/01160 A2 | 1/1998 |
| WO | WO 00/09086 A2 | 2/2000 |
| WO | WO 03/035244 A1 | 5/2003 |
| WO | WO 03/092739 A1 | 11/2003 |
| WO | WO 03/092740 A1 | 11/2003 |
| WO | WO 03/028323 A1 | 3/2006 |
| WO | WO 2009/039657 A1 | 4/2009 |

OTHER PUBLICATIONS

Dalwadi et al (Pharmaceutical Research, 22(12):2152-2162, 2005.*
Köping-Höggård et al., Gene Therapy, 2001, vol. 8, pp. 1108-1121.*
Dalwadi, et al. "Comparison of diafiltration and tangential flow filtration for purification of nano particle suspensions," Pharmaceutical Research (2005) 22(22):2152-2162.
Kopping-Hoggard, M., et al., "Chitosan as a nonviral gene delivery system. Structure-property relationships and charactersistics compared with polyethylenimine in virtro and after lung administration in vivo," Gene Therapy 8(14):1108-21 (2001).

* cited by examiner

*Primary Examiner* — Janet L Epps-Smith
(74) *Attorney, Agent, or Firm* — Todd A. Lorenz

(57) ABSTRACT

The invention provides highly concentrated chitosan-nucleic acid polyplex compositions and dispersions, and methods for producing the compositions and dispersions. Methods of mixing the chitosan-nucleic acid polyplexes include an inline mixing of chitosan solution and nucleic acid solution, followed by further concentrating the dispersion of chitosan-nucleic acid polyplexes, optionally with an aggregation inhibitor. Further provides are methods for altering the diameter of chitosan-nucleic acid polyplexes.

20 Claims, 7 Drawing Sheets

Figure 1: Process Block for 1L In-line Mixing Batch and Concentration

Figure 2: Small-Scale In-line Mixing

Figure 3: Mid-Scale In-line Mixing Schematic for 10L

Figure 4: TFF Concentration

Figure 5: In vitro Transfection of Mid-Scale Polyplex Mixed at Different Rates ered methods for producing chitosan-nucleic acid polyplexes by inline mixing processes that do not require static or dynamic mixers and are improved by non-inclusion of the same. Further, these methods can be used to prepare stable polyplexes that have a charge (i.e., zeta potential) that departs significantly from neutral. Surprisingly, the inventors have also found that particle size and uniformity may be controlled by altering feedstock volumes for inline mixing without altering the mixing ratio of DNA to chitosan or substantially altering the concentrations of DNA and chitosan in a mixing solution.

HIGH CONCENTRATION CHITOSAN-NUCLEIC ACID POLYPLEX COMPOSITIONS

CROSS-REFERENCE TO RELATED APPLICATIONS

This application claims the benefit of U.S. Ser. No. 60/976,376 filed 28 Sep. 2007, which is incorporated herein in its entirety by reference.

FIELD

The invention relates to homogeneous chitosan-nucleic acid polyplexes. The invention further relates to methods for concentrating chitosan-nucleic acid polyplexes in solution, and highly concentrated preparations of homogenous chitosan-nucleic acid polyplexes.

BACKGROUND

Chitosan is a non-toxic cationic copolymer of N-acetyl-D-glucosamine and D-glucosamine. Chitosan can form a complex with nucleic acid and has been used as a DNA delivery vehicle to transfect cells.

There is difficulty in producing a concentrated solution of chitosan-nucleic acid complexes. Increasing the concentrations of chitosan and nucleic acid in a mixing solution leads to precipitation as well as undesirable variation in the size of chitosan-nucleic acid complexes so produced. Additionally, increasing the concentration of chitosan-nucleic acid complexes in a prepared solution leads to the aggregation of complexes and precipitation from solution.

The use of concurrent flow mixing to produce uniform particles comprising DNA and condensing agents (e.g., polycationic carbohydrates) has been described (U.S. Pat. No. 6,537,813). To produce such particles, DNA solution and condensing agent solution may be concurrently and separately introduced into a flow through mixer that comprises a static or dynamic mixer which provides for mixing and particle formation. Maintaining the proper ratio of DNA and condensing agent throughout the introduction and mixing processes is reportedly important and a significant deviation from charge neutrality can lead to either incomplete condensation or particle aggregation in the process.

SUMMARY OF INVENTION

The present inventors have overcome obstacles in the field to produce highly concentrated chitosan-nucleic acid polyplex compositions, which find many applications in research and medicine. In preferred embodiments, the compositions comprise polyplexes of uniform size that do not aggregate or precipitate despite a high concentration, and exhibit stability under a variety of conditions. Further, preferred compositions of the invention are also isotonic as formed. Achieving isotonicity, while maintaining polyplex stability, is highly desirable for pharmaceutical and therapeutic applications. In addition, the inventors have discovered methods for producing chitosan-nucleic acid polyplexes by inline mixing processes that do not require static or dynamic mixers and are improved by non-inclusion of the same. Further, these methods can be used to prepare stable polyplexes that have a charge (i.e., zeta potential) that departs significantly from neutral. Surprisingly, the inventors have also found that particle size and uniformity may be controlled by altering feedstock volumes for inline mixing without altering the mixing ratio of DNA to chitosan or substantially altering the concentrations of DNA and chitosan in a mixing solution.

Accordingly, in one aspect, the invention provides compositions comprising hydrated chitosan-nucleic acid polyplexes. The compositions are highly concentrated in chitosan-nucleic acid polyplexes, having a nucleic acid concentration greater than about 0.5 mg/ml, wherein the composition is substantially free of precipitated polyplex.

In a preferred embodiment, the composition is a dispersion comprising chitosan-nucleic acid polyplex particles.

In a preferred embodiment, the composition is isotonic. In other embodiments, the composition may be hypertonic or hypotonic.

In a preferred embodiment, the composition has a nucleic acid concentration of at least about 0.6 mg/ml, more preferably at least about 0.75 mg/ml, more preferably at least about 1.0 mg/ml, more preferably at least about 1.2 mg/ml, and most preferably at least about 1.5 mg/ml.

In a preferred embodiment, the composition additionally comprises an aggregation inhibitor. In a preferred embodiment, the aggregation inhibitor is a sugar, preferably sucrose.

In a preferred embodiment, the composition comprises a counter anion concentration of less than about 80 mM, more preferably less than about 60 mM, more preferably less than about 40 mM, more preferably less than about 20 mM. Preferably the counter anion is acetate ion.

In a preferred embodiment, the chitosan-nucleic acid polyplexes of the composition have an average polydispersity index ("PDI") of less than about 0.5, more preferably less than about 0.4, more preferably less than about 0.3, more preferably less than about 0.2.

In a preferred embodiment, the polyplexes have an N:P ratio of at least about 2:1, more preferably at least about 5:1, more preferably at least about 10:1, more preferably at least about 15:1, more preferably at least about 20:1.

In a preferred embodiment, the polyplexes comprise chitosan molecules having on average less than about 3000, more preferably less than about 2000, more preferably less than about 1500, more preferably less than about 1000, more preferably less than about 500, more preferably less than about 100, more preferably less than about 50 glucosamine monomer units.

In a preferred embodiment, the polyplexes comprise chitosan that has an average molecular weight of less than about 500 kDa, more preferably less than about 250 kDa, more preferably less than about 150 kDa, more preferably less than about 100 kDa, more preferably less than about 50 kDa, more preferably less than about 25 kDa.

In a preferred embodiment, the polyplexes of the composition have an average diameter of less than about 750 nm, more preferably less than about 500 nm, more preferably less than about 250 nm, more preferably less than about 200 nm, and most preferably less than about 150 nm.

In a preferred embodiment, the composition consists essentially of chitosan-nucleic acid polyplexes and an aggregation inhibitor.

In another preferred embodiment, the composition consists essentially of chitosan-nucleic acid polyplexes.

In one aspect, the invention provides methods for concentrating dispersions of chitosan-nucleic acid polyplexes. The methods comprise providing a non-concentrated dispersion of chitosan-nucleic acid polyplexes and concentrating the non-concentrated dispersion of chitosan-nucleic acid polyplexes using concentrating means, preferably tangential flow filtration, to produce a concentrated dispersion of chitosan-nucleic acid polyplexes. Preferably the non-concentrated dispersion comprises an aggregation inhibitor. This concentrating process substantially increases the concentration of the chitosan-nucleic acid complexes while substantially maintaining the concentration of small molecules (e.g., aggregation inhibitor) thereby resulting in a composition that is concentrated in chitosan-nucleic acid complexes.

In a preferred embodiment, the concentrating means concentrates the dispersion by at least 2 fold, more preferably at least 5 fold, more preferably at least 6 fold, more preferably at least 7 fold, more preferably at least 8 fold, more preferably at least 9 fold, and most preferably at least 10 fold.

In a preferred embodiment, the aggregation inhibitor is a sugar, preferably sucrose.

In a preferred embodiment, the non-concentrated dispersion of chitosan-nucleic acid polyplexes comprises counter anion, preferably acetate ion, and the concentrating means does not selectively concentrate the counter anion. The counter anion enrichment is not as great as the nucleic acid enrichment in the concentrated dispersion. Preferably, the concentrated dispersion has a counter anion concentration not substantially greater than that of the non-concentrated dispersion.

In a preferred embodiment, the concentration of nucleic acid in the concentrated dispersion is at least about 0.5 mg/ml, more preferably at least about 0.6 mg/ml, more preferably at least about 0.75 mg/ml, more preferably at least about 1.0 mg/ml, more preferably at least about 1.2 mg/ml, and most preferably at least about 1.5 mg/ml.

In a preferred embodiment, inline mixing is used to prepare the non-concentrated dispersion of chitosan-nucleic acid polyplexes.

In a preferred embodiment, the non-concentrated dispersion has a volume of at least 10 mL, more preferably at least about 50 mL, more preferably at least about 500 mL, more preferably at least about 1 L, more preferably at least about 2 L, more preferably at least about 3 L, more preferably at least about 4 L, more preferably at least about 5 L, more preferably at least about 10 L.

In a preferred embodiment, the chitosan-nucleic acid polyplexes of the non-concentrated dispersion have an average PDI of less than about 0.5, more preferably less than about 0.4, more preferably less than about 0.3, more preferably less than about 0.2.

In a preferred embodiment, the chitosan-nucleic acid polyplexes of the concentrated dispersion have an average PDI of less than about 0.5, more preferably less than about 0.4, more preferably less than about 0.3, more preferably less than about 0.2.

In a preferred embodiment, the polyplexes have an N:P ratio of at least about 2:1, more preferably at least about 5:1, more preferably at least about 10:1, more preferably at least about 15:1, more preferably at least about 20:1.

In a preferred embodiment, the polyplexes comprise chitosan molecules having on average less than about 3000, more preferably less than about 2000, more preferably less than about 1500, more preferably less than about 1000, more preferably less than about 500, more preferably less than about 100, more preferably less than about 50 glucosamine monomer units.

In a preferred embodiment, the polyplexes comprise chitosan that has an average molecular weight of less than about 500 kDa, more preferably less than about 250 kDa, more preferably less than about 150 kDa, more preferably less than about 100 kDa, more preferably less than about 50 kDa, more preferably less than about 25 kDa.

In a preferred embodiment, the polyplexes of the composition have an average diameter of less than about 750 nm, more preferably less than about 500 nm, more preferably less than about 250 nm, more preferably less than about 200 nm, and most preferably less than about 150 nm.

In one aspect, the invention provides concentrated dispersions of chitosan nucleic acid polyplexes produced by methods disclosed herein.

In one aspect, the invention provides methods for modulating the properties of chitosan-nucleic acid polyplexes formed by mixing chitosan and nucleic acid solutions. In one embodiment, the invention provides methods for modulating chitosan-nucleic acid polyplex diameter. In another embodiment, the invention provides methods for modulating chitosan-nucleic acid polyplex zeta potential. The methods involve altering the volume of chitosan or nucleic acid solution used to produce the polyplexes, without altering the ratio of nucleic acid to chitosan, or the concentration of nucleic acid and chitosan in a mixing solution. In a preferred embodiment, the methods involve inline mixing of chitosan and nucleic acid feedstock solutions.

In one aspect, the invention provides pharmaceutical compositions comprising hydrated chitosan-nucleic acid polyplexes and having a nucleic acid concentration greater than about 0.5 mg/ml, wherein the chitosan-nucleic acid polyplexes comprise a therapeutic nucleic acid construct.

In a preferred embodiment, pharmaceutical compositions have a nucleic acid concentration of at least about 0.6 mg/ml, more preferably at least about 0.75 mg/ml, more preferably at least about 1.0 mg/ml, more preferably at least about 1.2 mg/ml, and most preferably at least about 1.5 mg/ml.

In a preferred embodiment, the pharmaceutical composition comprises an aggregation inhibitor. In a preferred embodiment, the aggregation inhibitor is a sugar, preferably sucrose.

In a preferred embodiment, the pharmaceutical composition has a counter anion concentration less than about 80 mM, more preferably less than about 60 mM, more preferably less than about 40 mM, more preferably less than about 20 mM. Preferably the counter anion is acetate ion.

In a preferred embodiment, the pharmaceutical composition is isotonic. In other embodiments, the pharmaceutical composition may be hypertonic or hypotonic.

In one aspect, the invention provides a method for preparing concentrated chitosan-nucleic acid polyplex dispersions, comprising inline mixing chitosan and nucleic acid solutions to form a non-concentrated chitosan-nucleic acid dispersion, followed by concentrating the non-concentrated chitosan nucleic acid dispersion using TFF, to produce a concentrated chitosan-nucleic acid polyplex dispersion.

In a preferred embodiment, TFF concentrates the dispersion by at least 2 fold, more preferably at least 5 fold, more preferably at least 6 fold, more preferably at least 7 fold, more preferably at least 8 fold, more preferably at least 9 fold, and most preferably at least 10 fold.

In a preferred embodiment, the concentration of nucleic acid in the concentrated dispersion is at least about 0.5 mg/ml, more preferably at least about 0.6 mg/ml, more preferably at least about 0.75 mg/ml, more preferably at least about 1.0 mg/ml, more preferably at least about 1.2 mg/ml, and most preferably at least about 1.5 mg/ml.

In a preferred embodiment, the concentrated dispersion has a counter anion concentration less than about 80 mM, more preferably less than about 60 mM, more preferably less than about 40 mM, more preferably less than about 20 mM. Preferably the counter anion is acetate ion.

Preferably the concentrated dispersion comprises an aggregation inhibitor. Preferably the aggregation inhibitor is a sugar, preferably sucrose.

Preferably the concentrated dispersion is isotonic. In other embodiments, the concentrated dispersion may be hypertonic or hypotonic.

DETAILED DESCRIPTION

Figure 1:
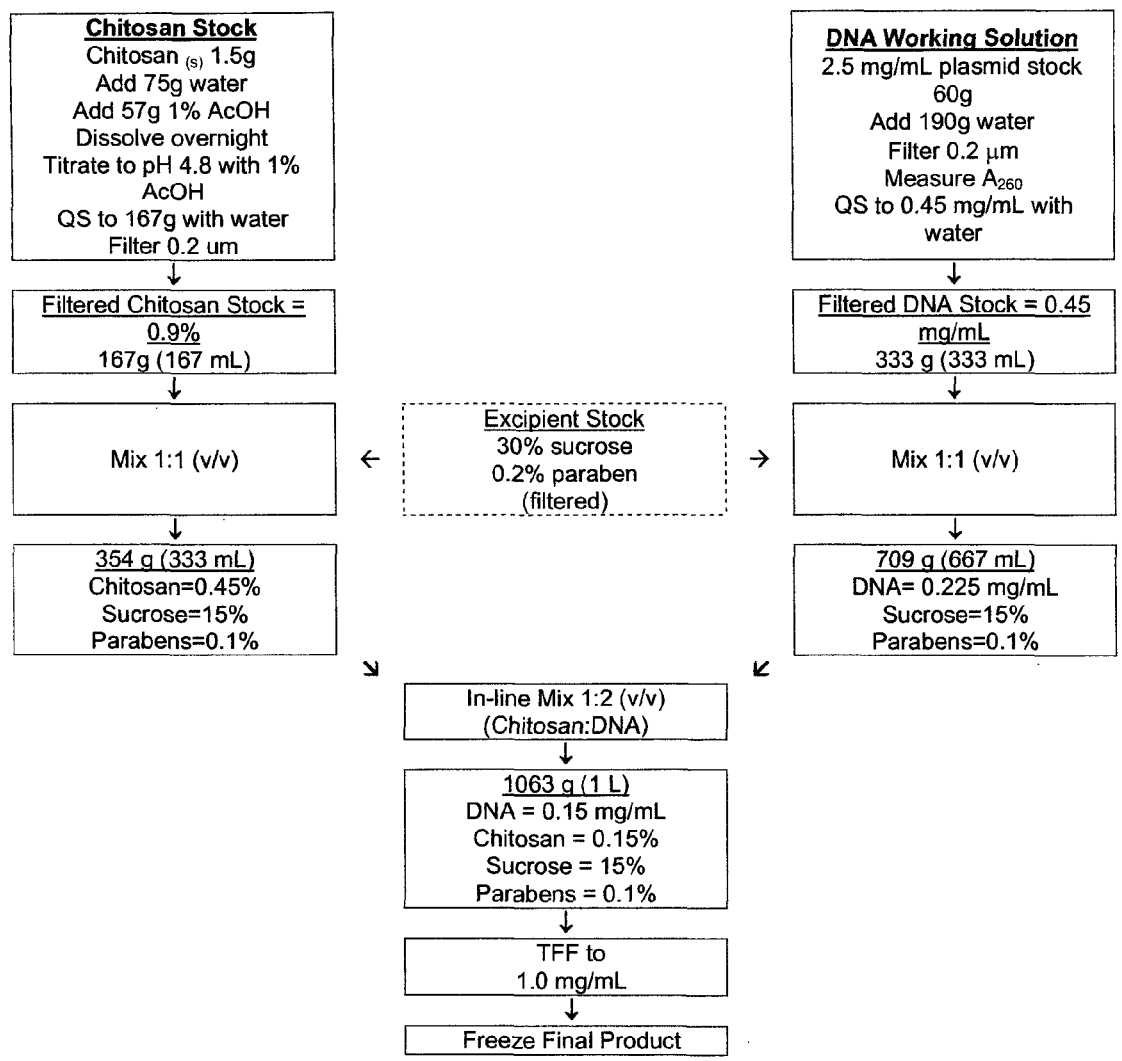
FIG. 1. Schematic drawing of a typical process block for manufacturing a 1 L batch of chitosan-nucleic acid polyplex dispersion followed by TFF concentration is shown.

By "chitosan-nucleic acid polyplex", "chitosan-nucleic acid polyplex particles" or "polyplex" is meant a complex comprising a plurality of chitosan molecules (each a polymer of glucosamine monomers) and a plurality of nucleic acid molecules. Chitosan monomers include derivatives, including chitosan with attached ligand. "Derivatives" will be understood to include the broad category of chitosan-based polymers comprising covalently modified N-acetyl-D-glucosamine and/or D-glucosamine units, as well as chitosan-based polymers incorporating other units, or attached to other moieties. Derivatives are frequently based on a modification of the hydroxyl group or the amine group of glucosamine. Examples of chitosan derivatives include, but are not limited to, trimethylated chitiosan, PEGylated chitosan, thiolated chitosan, galactosylated chitosan, alkylated chitosan, PEI-incorprated chitosan, arginine modified chitosan, uronic acid modified chitosan, and the like. For further teaching on chitosan derivatives, see, for example, pp. 63-74 of "Non-viral Gene Therapy", K. Taira, K. Kataoka, T. Niidome (editors), Springer-Verlag Tokyo, 2005, ISBN 4-431-25122-7; Zhu et al., Chinese Science Bulletin, December 2007, vol. 52 (23), pp. 3207-3215; and Varma et al., Carbohydrate Polymers 55 (2004) 77-93.

As used herein, "average weight" of chitosan polymers refers to the weight average molecular weight.

By "counter anion" is meant an anion capable of electrostatic interaction with a charged chitosan amine. Preferred counter anions include acetate ion and chloride ion.

Chitosan may be prepared as disclosed in U.S. Ser. No. 11/694,852 filed 30 Mar. 2007, which is expressly incorporated herein in its entirety by reference. Chitosan derivatives may also be used, including chitosan derivatives comprising a ligand moiety.

Chitosan-Nucleic Acid Polyplex Compositions

In one aspect, the invention provides chitosan-nucleic acid polyplex compositions, comprising hydrated chitosan-nucleic acid polyplexes. The compositions are highly concentrated in chitosan-nucleic acid polyplexes, having a nucleic acid concentration greater than about 0.5 mg/ml. The compositions are substantially free of polyplex precipitate. As used herein, "substantially free" of polyplex precipitate means that the composition is essentially free from particles that can be observed on visual inspection.

In a preferred embodiment, the chitosan-nucleic acid polyplex composition has a nucleic acid concentration of at least about 0.6 mg/ml, more preferably at least about 0.75 mg/ml, more preferably at least about 1 mg/ml, more preferably at least about 1.2 mg/ml, and most preferably at least about 1.5 mg/ml. In a preferred embodiment, the composition is substantially free of uncomplexed nucleic acid.

In a preferred embodiment, the chitosan-nucleic acid polyplex compositions are dispersions. In a preferred embodiment, the dispersion is isotonic. Achieving isotonicity, while maintaining polyplex stability, is highly desirable in formulating pharmaceutical compositions, and these preferred compositions are well suited to pharmaceutical formulation and therapeutic applications.

In other embodiments, the composition may be hypertonic or hypotonic.

In a preferred embodiment, the chitosan-nucleic acid polyplex composition additionally comprises an aggregation inhibitor. The aggregation inhibitor is an agent that partially or completely reduces polyplex aggregation and/or precipitation and provides for concentrating chitosan-nucleic acid polyplexes by concentrating means, preferably through the use of tangential flow filtration ("TFF"). A highly preferred aggregation inhibitor is sucrose, though other aggregation inhibitors, such as other sugars that are capable of reducing polyplex precipitation and which provide for concentrating chitosan-nucleic acid polyplexes may be used. Examples of other aggregation inhibitors include, but are not limited to, trehalose, glycerol, fructose, glucose, and other reducing and non-reducing sugars.

In a preferred embodiment, the aggregation inhibitor used is sucrose. The concentration of sucrose in the chitosan-nucleic acid polyplex dispersion is preferably between about 3% and 20% by weight. Most preferably the concentration of sucrose provides for an isotonic composition.

The chitosan-nucleic acid polyplex composition is preferably homogeneous in respect of polyplex size. Accordingly, in a preferred embodiment, the chitosan-nucleic acid polyplexes of the composition have a low average polydispersity index ("PDI"). In an especially preferred embodiment, the chitosan-nucleic acid polyplex dispersion has a PDI of less than about 0.5, more preferably less than about 0.4, more preferably less than about 0.3, more preferably less than about 0.2.

The chitosan-nucleic acid polyplexes are preferably substantially size stable in the composition. In a preferred embodiment, a composition of the invention comprises polyplexes that increase in average diameter by less than 100%, more preferably less than 50%, more preferably less than 25%, at room temperature for 6 hours, more preferably 12 hours, more preferably 24 hours, more preferably 48 hours.

The chitosan-nucleic acid polyplexes are preferably substantially size stable under cooled conditions. In a preferred embodiment, a composition of the invention comprises polyplexes that increase in average diameter by less than 100%, more preferably less than 50%, more preferably less than 25%, at 2-8° degrees Celsius for 6 hours, more preferably 12 hours, more preferably 24 hours, more preferably 48 hours.

The chitosan-nucleic acid polyplexes of compositions are preferably substantially size stable under freeze-thaw conditions. In a preferred embodiment, a composition of the invention comprises polyplexes that increase in average diameter by less than 100%, more preferably less than 50%, more preferably less than 25% at room temperature for 6 hours, more preferably 12 hours, more preferably 24 hours, more preferably 48 hours following thaw from frozen at −20 to −80 degrees Celsius.

The chitosan-nucleic acid polyplexes comprise a nucleic acid component and a chitosan component. A nucleic acid of the present invention will generally contain phosphodiester bonds, although in some cases nucleic acid analogs are included that may have alternate backbones or other modifications or moieties incorporated for any of a variety of purposes, e.g., stability and protection. Other analog nucleic acids contemplated include those with non-ribose backbones. In addition, mixtures of naturally occurring nucleic acids, analogs, and both can be made. The nucleic acids may be single stranded or double stranded or contain portions of both double stranded or single stranded sequence. Nucleic acids include but are not limited to DNA, RNA and hybrids where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. Nucleic acids include DNA in any form, RNA in any form, including triplex, duplex or single-stranded, anti-sense, siRNA, ribozymes, deoxyribozymes, polynucleotides, oligonucleotides, chimeras, and derivatives thereof.

In one embodiment, the nucleic acid component comprises a therapeutic nucleic acid. Therapeutic nucleic acids include therapeutic RNAs, which are RNA molecules capable of exerting a therapeutic effect in a mammalian cell. Therapeutic RNAs include antisense RNAs, siRNAs, short hairpin RNAs, and enzymatic RNAs. Therapeutic nucleic acids include nucleic acids intended to form triplex molecules, protein binding nucleic acids, ribozymes, deoxyribozymes, and small nucleotide molecules.

Therapeutic nucleic acids also include nucleic acids encoding therapeutic proteins, including cytotoxic proteins and prodrugs; ribozymes; antisense or the complement thereof; or other such molecules.

In a preferred embodiment, the nucleic acid component comprises a therapeutic nucleic acid construct. The therapeutic nucleic acid construct is a nucleic acid construct capable of exerting a therapeutic effect. Therapeutic nucleic acid constructs may comprise nucleic acids encoding therapeutic proteins, as well as nucleic acids that produce transcripts that are therapeutic RNAs. A therapeutic RNA is an RNA molecule capable of exerting a therapeutic effect in a mammalian cell. Therapeutic RNAs include antisense RNAs, siRNAs, short hairpin RNAs, and enzymatic RNAs. Therapeutic nucleic acids include nucleic acids intended to form triplex molecules, protein binding nucleic acids, ribozymes, deoxyribozymes, and small nucleotide molecules. A therapeutic nucleic acid may be used to effect genetic therapy by serving as a replacement or enhancement for a defective gene or to compensate for lack of a particular gene product, by encoding a therapeutic product. A therapeutic nucleic acid may also inhibit expression of an endogenous gene. A therapeutic nucleic acid may encode all or a portion of a translation product, and may function by recombining with DNA already present in a cell, thereby replacing a defective portion of a gene. It may also encode a portion of a protein and exert its effect by virtue of co-suppression of a gene product. In a preferred embodiment, the therapeutic nucleic acid is selected from those disclosed in U.S. Ser. No. 11/694,852.

In a preferred embodiment, the polyplexes comprise chitosan molecules having on average less than about 3000, more preferably less than about 2000, more preferably less than about 1500, more preferably less than about 1000, more preferably less than about 500, more preferably less than about 100, more preferably less than about 50 glucosamine monomer units.

In a preferred embodiment, the polyplexes comprise chitosan that has an average weight of less than about 500 kDa, more preferably less than about 250 kDa, more preferably less than about 150 kDa, more preferably less than about 100 kDa, more preferably less than about 50 kDa, more preferably less than about 25 kDa.

In a preferred embodiment, the polyplexes of the composition have an average diameter of less than 750 nm, more preferably less than 500 nm, more preferably less than about 250 nm, more preferably less than about 200 nm, and most preferably less than about 150 nm.

In one embodiment, the chitosan components have an average molecular weight between 3 kDa and 250 kDa.

In one embodiment, the chitosan components have an average molecular weight greater than or equal to 250 kDa.

In one embodiment, the chitosan components have an average molecular weight less than or equal to 3 kDa.

In one embodiment, the chitosan-nucleic acid polyplexes have an N:P ratio between about 2:1 and about 100:1, more preferably about 5:1 and about 90:1, more preferably about 10:1 and about 90:1.

In one embodiment, the chitosan-nucleic acid polyplexes have an N:P ratio greater than or equal to 90:1.

In one embodiment, the chitosan-nucleic acid polyplexes have an N:P ratio less than or equal to 10:1.

In one embodiment, the chitosan-nucleic acid polyplexes have an average zeta potential between +30 mV and +50 mV at a pH of 5.

In one embodiment, the chitosan-nucleic acid polyplexes have an average zeta potential less than or equal to +30 mV at a pH of 5.

In one embodiment, the chitosan-nucleic acid polyplexes have an average zeta potential greater than or equal to +50 mV at a pH of 5.

In one embodiment, the chitosan-nucleic acid polyplexes have an average diameter less than 225 nm.

In one embodiment, the chitosan-nucleic acid polyplexes have an average diameter greater than or equal to 225 nm.

In one embodiment, the composition has a pH of less than 6.5, more preferably less than 6.0, and most preferably between about 4.5 and about 5.5.

In one embodiment, the composition has a pH greater than or equal to 6.5.

In one embodiment, the composition has a pH less than or equal to 4.5.

In one embodiment, the chitosan molecules of the polyplex have a degree of deacetylation greater than about 70%, more preferably greater than about 75%, more preferably greater than about 80%, more preferably greater than about 85%, more preferably greater than about 90%, more preferably greater than about 95%, and most preferably at least 98%.

In one embodiment, the chitosan molecules of the polyplex have a degree of deacetylation less than or equal to 70%.

In a preferred embodiment, the composition consists essentially of chitosan-nucleic acid polyplexes and an aggregation inhibitor. Such composition may include counter anion and other excipients, e.g., parabens.

In another preferred embodiment, the composition consists essentially of chitosan-nucleic acid polyplexes. Such composition may include counter anion and other excipients, e.g., parabens.

In an especially preferred embodiment, the chitosan-nucleic acid polyplex is selected from those disclosed in U.S. Ser. No. 11/694,852.

Methods of Preparation

In a preferred embodiment, a high concentration chitosan-nucleic acid polyplex composition of the invention is produced by concentrating a non-concentrated dispersion of chitosan-nucleic acid polyplexes.

A non-concentrated chitosan-nucleic acid polyplex composition preferably has a nucleic acid concentration less than 0.5 mg/ml.

The non-concentrated dispersion of chitosan-nucleic acid polyplexes is preferably prepared by inline mixing, though other methods, such as forming a mixing solution by dripping nucleic acid or chitosan solution into the other may be used. However, inline mixing provides for the preparation of a large volume of homogeneous chitosan-nucleic acid polyplexes, preferably having an average PDI, preferably less than 0.5, more preferably less than about 0.4, more preferably less than about 0.3, more preferably less than about 0.2.

In-line mixing is a well-known process whereby two (or more) fluid streams are brought together into a single stream. In-line mixing is exemplified below. For additional disclosure on inline mixing see, for example, U.S. Pat. Nos. 6,251,599 and 6,537,813, each of which is expressly incorporated herein in its entirety by reference.

While mixers such as static mixers and dynamic mixers may be used, such devices lead to an increased PDI of complexes formed by the present methods. Accordingly, in preferred embodiments of the present invention, inline mixing is done without the use of such mixers.

In the present invention, tangential flow filtration ("TFF") is the preferred means for concentrating a non-concentrated dispersion of chitosan-nucleic acid polyplexes. In TFF operation, a chitosan-nucleic acid polyplex dispersion is pumped across the surface of a semi-permeable membrane while pressure is applied toward the membrane to force a portion of the fluid through the membrane. Molecules that are smaller than the membrane pores are transported through the membrane pores and collected as permeate. Permeating solutes include but are not limited to salts, ions, sugars and microbial preservatives. Molecular entities that are too large to pass through the membrane pores, including the chitosan-nucleic acid polyplex, are retained in the stream and re-circulated as retentate. Using TFF, polyplex concentration may be increased many fold, the result being a highly concentrated polyplex dispersion. In a preferred embodiment, the highly concentrated polyplex dispersion is isotonic.

In a preferred embodiment, a non-concentrated chitosan-nucleic acid polyplex dispersion comprises a sugar, preferably sucrose. As described below, it was found that sucrose is an aggregation inhibitor that prevents aggregation of particles during the concentration process. Additionally, sucrose is an effective cryoprotectant, and exemplary frozen polyplex dispersions with DNA concentration of about 1 mg/mL and containing up to 15% sucrose are stable for up to at least 1 month.

The use of TFF to concentrate non-concentrated chitosan-nucleic acid polyplexes is exemplified below.

Altering Chitosan-Nucleic Acid Polyplex Properties by Manipulating Feedstock Volume It has been surprisingly found that the properties of chitosan-nucleic acid polyplexes formed by mixing nucleic acid and chitosan can be modulated while maintaining a substantially constant chitosan:nucleic acid ratio and maintaining a substantially constant mixing concentration of chitosan and nucleic acid. In particular, it has been found that by altering the volume ratio of chitosan and nucleic acid feedstock solutions, the properties of resultant polyplexes formed by mixing the two solutions may be altered.

Accordingly, in one aspect, the invention provides methods for modulating the properties of chitosan-nucleic acid polyplexes formed by mixing chitosan and nucleic acid solutions. In one embodiment, the invention provides methods for modulating chitosan-nucleic acid polyplex diameter. In another embodiment, the invention provides methods for modulating chitosan-nucleic acid polyplex zeta potential. The methods involve altering the volume of chitosan or nucleic acid solution used to produce the polyplexes, without substantially altering the ratio of nucleic acid to chitosan or the concentration of nucleic acid and chitosan in a mixing solution. In a preferred embodiment, the methods involve inline mixing of chitosan and nucleic acid feedstock solutions.

Powdered Formulations

The chitosan-nucleic acid polyplex compositions of the invention include powders. In a preferred embodiment, the invention provides a dry powder chitosan-nucleic acid polyplex composition. In a preferred embodiment, the dry powder chitosan-nucleic acid polyplex composition is produced through the dehydration of a chitosan-nucleic acid polyplex dispersion of the invention.

Methods of Use

In addition to therapeutic applications, the present invention is generally useful whenever stabilization of nucleic acid is desired and increased concentration of nucleic acid is desired (for example, for increased transfection efficiency). In a laboratory setting, the stability of nucleic acid is important whenever procedures are being performed which compromise the structural integrity and functionality of nucleic acid.

Pharmaceutical Formulations

The present invention also provides "pharmaceutically acceptable" or "physiologically acceptable" formulations comprising chitosan-nucleic acid polyplex compositions of the invention. Such formulations can be administered in vivo to a subject in order to practice treatment methods.

As used herein, the terms "pharmaceutically acceptable" and "physiologically acceptable" refer to carriers, diluents, excipients and the like that can be administered to a subject, preferably without producing excessive adverse side-effects (e.g., nausea, abdominal pain, headaches, etc.). Such preparations for administration include sterile aqueous or non-aqueous solutions, suspensions, and emulsions.

Pharmaceutical formulations can be made from carriers, diluents, excipients, solvents, dispersion media, coatings, antibacterial and antifungal agents, isotonic and absorption delaying agents, and the like, compatible with administration to a subject. Such formulations can be contained in a tablet (coated or uncoated), capsule (hard or soft), microbead, emulsion, powder, granule, crystal, suspension, syrup or elixir. Supplementary active compounds and preservatives, among other additives, may also be present, for example, antimicrobials, anti-oxidants, chelating agents, and inert gases and the like.

A pharmaceutical formulation can be formulated to be compatible with its intended route of administration. For example, for oral administration, a composition can be incorporated with excipients and used in the form of tablets, troches, or capsules, e.g., gelatin capsules. Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or flavoring.

Formulations can also include carriers to protect the composition against rapid degradation or elimination from the body, such as a controlled release formulation, including implants and microencapsulated delivery systems. For example, a time delay material such as glyceryl monostearate or glyceryl stearate alone, or in combination with a wax, may be employed.

Suppositories and other rectally administrable formulations (e.g., those administrable by enema) are also contemplated. Further regarding rectal delivery, see, for example, Song et al., *Mucosal drug delivery: membranes, methodologies, and applications*, Crit. Rev. Ther. Drug. Carrier Syst., 21:195-256, 2004; Wearley, Recent progress in protein and peptide delivery by noninvasive routes, Crit. Rev. Ther. Drug. Carrier Syst., 8:331-394, 1991.

Additional pharmaceutical formulations appropriate for administration are known in the art and are applicable in the methods and compositions of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; and Pharmaceutical Principles of Solid Dosage Forms, Technonic Publishing Co., Inc., Lancaster, Pa., (1993)).

Administration

Any of a number of administration routes are possible and the choice of a particular route will in part depend on the target tissue. Syringes, endoscopes, cannulas, intubation tubes, catheters and other articles may be used for administration.

The doses or "effective amount" for treating a subject are preferably sufficient to ameliorate one, several or all of the symptoms of the condition, to a measurable or detectable extent, although preventing or inhibiting a progression or worsening of the disorder or condition, or a symptom, is a satisfactory outcome. Thus, in the case of a condition or disorder treatable by expressing a therapeutic nucleic acid in target tissue, the amount of therapeutic RNA or therapeutic protein produced to ameliorate a condition treatable by a method of the invention will depend on the condition and the desired outcome and can be readily ascertained by the skilled artisan. Appropriate amounts will depend upon the condition treated, the therapeutic effect desired, as well as the individual subject (e.g., the bioavailability within the subject, gender, age, etc.). The effective amount can be ascertained by measuring relevant physiological effects.

Veterinary applications are also contemplated by the present invention. Accordingly, in one embodiment, the invention provides methods of treating non-human mammals, which involve administering a chitosan-based nanoparticle of the invention to a non-human mammal in need of treatment.

Oral Administration

The compounds of the invention may be administered orally. Oral administration may involve swallowing, so that the compound enters the gastrointestinal tract. Compositions of the invention may also be administered directly to the gastrointestinal tract.

Formulations suitable for oral administration include solid formulations such as tablets, capsules containing particulates, liquids, or powders, lozenges (including liquid-filled), chews, multi- and nano-particulates, gels, films, ovules, and sprays.

Liquid formulations include suspensions, solutions, syrups and elixirs. Liquid formulations may be prepared by the reconstitution of a solid.

Tablet dosage forms generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a film-forming polymer, a binder, a solvent, a humectant, a plasticiser, a stabiliser or emulsifier, a viscosity-modifying agent and a solvent. Some components of the formulation may perform more than one function.

Also included in the invention are multiparticulate beads comprising a composition of the invention.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Other suitable release technologies such as high energy dispersions and osmotic and coated particles are known.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents, but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions.

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle) from a dry powder inhaler or as an aerosol spray from a pressurised container, pump, spray, atomiser, or nebuliser, with or without the use of a suitable propellant.

Capsules, blisters and cartridges for use in an inhaler or insufflator may be formulated to contain a powder mix of the compound of the invention, a suitable powder base such as lactose or starch and a performance modifier such as I-leucine, mannitol, or magnesium stearate.

Formulations for inhaled/intranasal administration may be formulated to be immediate and/or modified release. Modified release formulations include delayed-, sustained-, pulsed-, controlled-, targeted and programmed release.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops. Other formulations suitable for ocular and aural administration include ointments, biodegradable (e.g. absorbable gel sponges, collagen) and non-biodegradable (e.g. silicone) implants, wafers, lenses and particulate systems. Formulations may also be delivered by iontophoresis.

Formulations for ocular/aural administration may be formulated to be immediate and/or modified release. Modified release formulations include delayed-, sustained-, pulsed-, controlled-, targeted, or programmed release.

EXPERIMENTAL

Example 1

Preparation of Polyplexes Up to 250 μg/mL Followed by Concentration to >1 mg/mL

See FIG. 1 and description below for exemplary descriptions of reagents, concentrations, and ratios.

A simple small-scale in-line mixing apparatus was tested using syringe pumps and high-speed peristaltic pumps, silicone tubing and polypropylene T-junctions. This process was used to make polyplexes with a final DNA concentration of up to 250 μg/mL at an N/P ratio of 20 using 23 mer/98% DDA chitosan (i.e., chitosan polymers having an average of 23 monomers (glucosamine), and 98% deacetylation). The results showed that particle size and PDI of the polyplexes could be tightly controlled by controlling the feedstock concentrations, volume mixing ratios, and flow rates of the DNA and chitosan solutions. In addition, it was found that incorporating sucrose in the DNA and chitosan feedstocks aided the fabrication process by reducing particle size and PDI. The inclusion of sucrose also prevented aggregation of particles during the concentration process. Frozen polyplexes with DNA concentration of about 1 mg/mL and containing up to 15% sucrose were stable for up to at least 1 month. Additionally, the in-line mixing process was easily scaled from 50 mL up to 2 L with low relative standard deviation (RSD) values: particle size=±9%, PDI=±6%.

| Material | Supplier | Catalogue # |
|---|---|---|
| Chitosan (23 mer, 98% DDA) | Biosyntech | N/A |
| pDNA (pCHS4-3xFLAG-CMV-SEAP-attB) | enGene Inc. | N/A |
| pDNA (pCMV-INT) | enGene Inc. | N/A |
| pDNA (gWIZ-SEAP) | Aldevron LLC | 5005 |
| pDNA (gWIZ-Luciferase) | Aldevron LLC | 5001 |
| Sucrose, ACS grade | Fisher Scientific | S5-3 |
| Pt-cured silicone tubing, 1/16" ID | Cole-Parmer | 95802-02 |
| PP Tee fittings, 3/32" ID | Cole-Parmer | 30623-57 |
| PP syringes, 3 mL | B-D | 309585 |
| PP syringes, 10 mL | B-D | 309604 |
| PP syringes, 20 mL | B-D | 309661 |
| PP syringes, 30 mL | B-D | 309650 |
| PP Luer fittings, 1/8" ID | Cole-Parmer | 45500-04 |
| Syringe filters 25-mm, 0.2 μm Supor membrane | Pall | 4612 |
| Syringe filters 32-mm, 0.2 μm Supor membrane | Pall | 4652 |
| Disposable cuvettes, PS, 1.5 mL semi-micro | Plastibrand | 759075D |
| Folded capillary Zeta cells | Malvern Instruments | DTS 1060 |
| TFF cartridge, 73 cm², 1 mm ID, 100K MWCO | GE Healthcare | 56-4101-14 |
| TFF cartridge, 850 cm², 1 mm ID, 100K MWCO | GE Healthcare | 56-4102-15 |
| TFF cartridge, 73 cm², 1 mm ID, 500K MWCO | GE Healthcare | 56-4101-18 |
| PicoGreen Quant-iT ds DNA HS assay kit | Invitrogen | Q32854 |
| EcoR1 enzyme, 20,000 U/mL | New England BioLabs | R0101S |
| EcoR1 buffer, 10X | New England BioLabs | B0101S |
| Chitosanase enzyme, 62 U/mL | Sigma | C0794 |
| Supercoiled DNA ladder | Invitrogen | 15622-012 |
| TrackIt Cyan/Yellow Loading Buffer, 6X | Invitrogen | 10482-035 |
| Ethidium Bromide | EM Science | 4410 |
| Agarose, Ultra-Pure | Invitrogen | 15510-027 |
| 293T-K cell line | Dr. Kieffer at UBC | N/A |
| Dulbecco's Modified Eagle Medium | VWR | X16777-128 |
| Fetal bovine serum | Wisent | 080150 |
| Penicillin/Streptomycin | Invitrogen | 15140-122 |
| Phosphate buffered saline | Invitrogen | 21600-010 |
| Trypsin | Invitrogen | 25300-062 |
| Opti-mem | Invitrogen | 31985-070 |
| SEAP chemiluminescent assay | Roche | 1779842 |
| Placental alkaline phosphatase enzyme | Sigma | P-3895 |
| Bovine serum albumin (BSA) | Sigma | A9418 |
| Glycerol | Sigma | G5516 |
| Microlite-1 white flat bottom 96-well plate | VWR | 7417 |

| Equipment | Manufacturer |
|---|---|
| Syringe pump, NE-1000 | New Era Pump Systems Inc. |
| Syringe pump, NE-1000 | New Era Pump Systems Inc. |
| Peristaltic Pumps, Materflex L/S pump drives with L/S Easy-Load II pumpheads | Cole Parmer |
| Particle Sizer, Zetasizer Nano (ZEN 3600) | Malvern Instruments |
| pH Meter, Accumet AB15 | Fisher Scientific |
| UV Spectrophotometer, Ultrospec 2100 pro | Biochrom Ltd. |
| Qubit Fluorometer, cat # Q32857 | Invitrogen |
| FluorChem Imaging System including AlphaEaseFC software v3.1 | Alpha Inotech Corp |
| Luminometer (LmaxII384) including Softmax Pro software v4.7.1 | Molecular Devices |
| Small-scale TFF System (MidGee) | GE Healthcare |
| Mid-scale TFF System (QuixStand) | GE-Healthcare |

Polyplex Naming Convention

The terms refer to the type of chitosan, N/P ratio, acetic acid content, pH and DNA concentration. An example with detailed description is given in Table 1.

TABLE 1

| Polyplex Formulation Naming Convention Example C(23,98)-N20-Ac6-pH4.8-c150 | | | | |
|---|---|---|---|---|
| C(23,98) | N20 | Ac6 | pH 4.8 | c150 |
| Chitosan (23 mer, 98% DDA) | NP ratio = 20 | AcOH = 6 mM | pH = 4.8 | DNA = 150 μg/mL |

In-Line Mixing Process Flow

A typical process block for manufacturing a 1 L batch followed by TFF concentration is shown in FIG. 1.

Small-Scale in-Line Mixing

Figure 2:
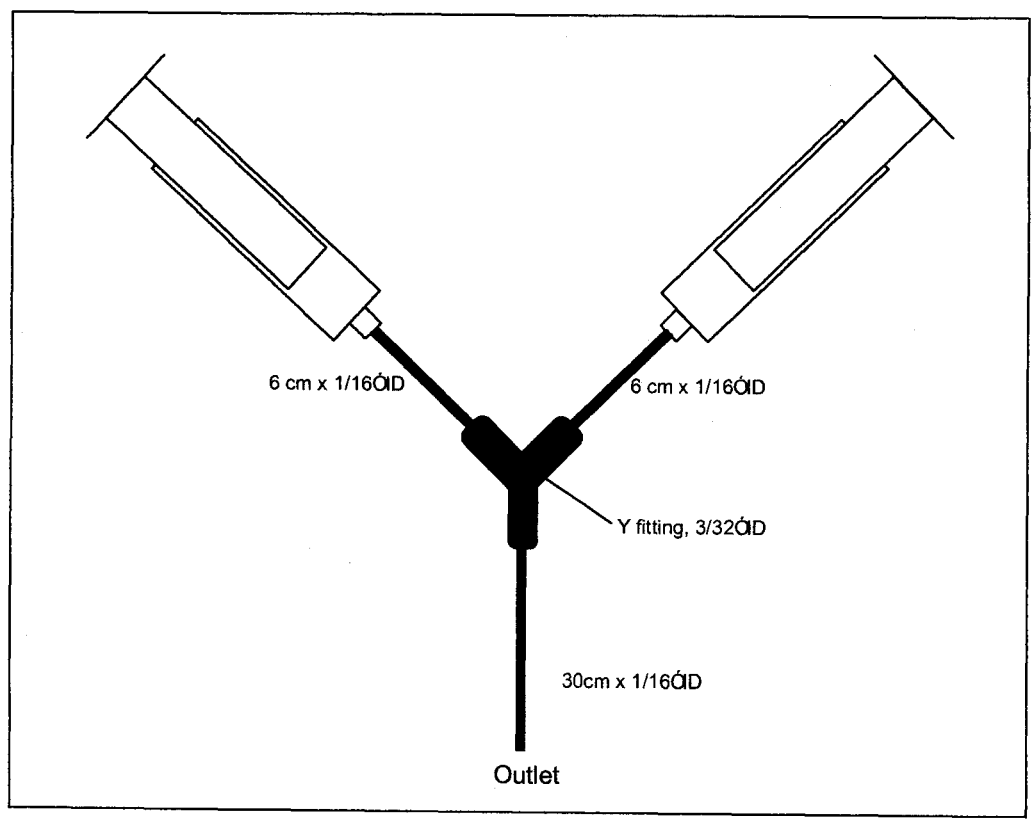
FIG. 2. Schematic drawing of small scale inline mixing process. Syringes are polypropylene latex-free and can be scaled up to 60 mL each. Two precision syringe pumps drive the syringes. Tubing is 1/16-inch ID platinum-cured silicone. Mixing junction shown is a Y, but may also be a T. Mixing junction material of construction is polypropylene.

A simple small-scale in-line mixing apparatus was tested using syringe pumps, 1/16-inch ID silicone tubing; and a 3/32-inch ID polypropylene junction in a T configuration. A schematic of the set-up with 3 mL capacity syringes is shown in FIG. 2. Note that the maximum syringe volume for this set-up is 60 mL. This process was used to make polyplexes with final DNA concentration of 150 μg/mL at an NP ratio of 20 using 24 mer/98% DDA chitosan. DNA and chitosan feedstocks were mixed at a volume ratio of 2:1 to produce uniform polyplex formulations.

Mid-Scale In-line Mixing

Figure 3:
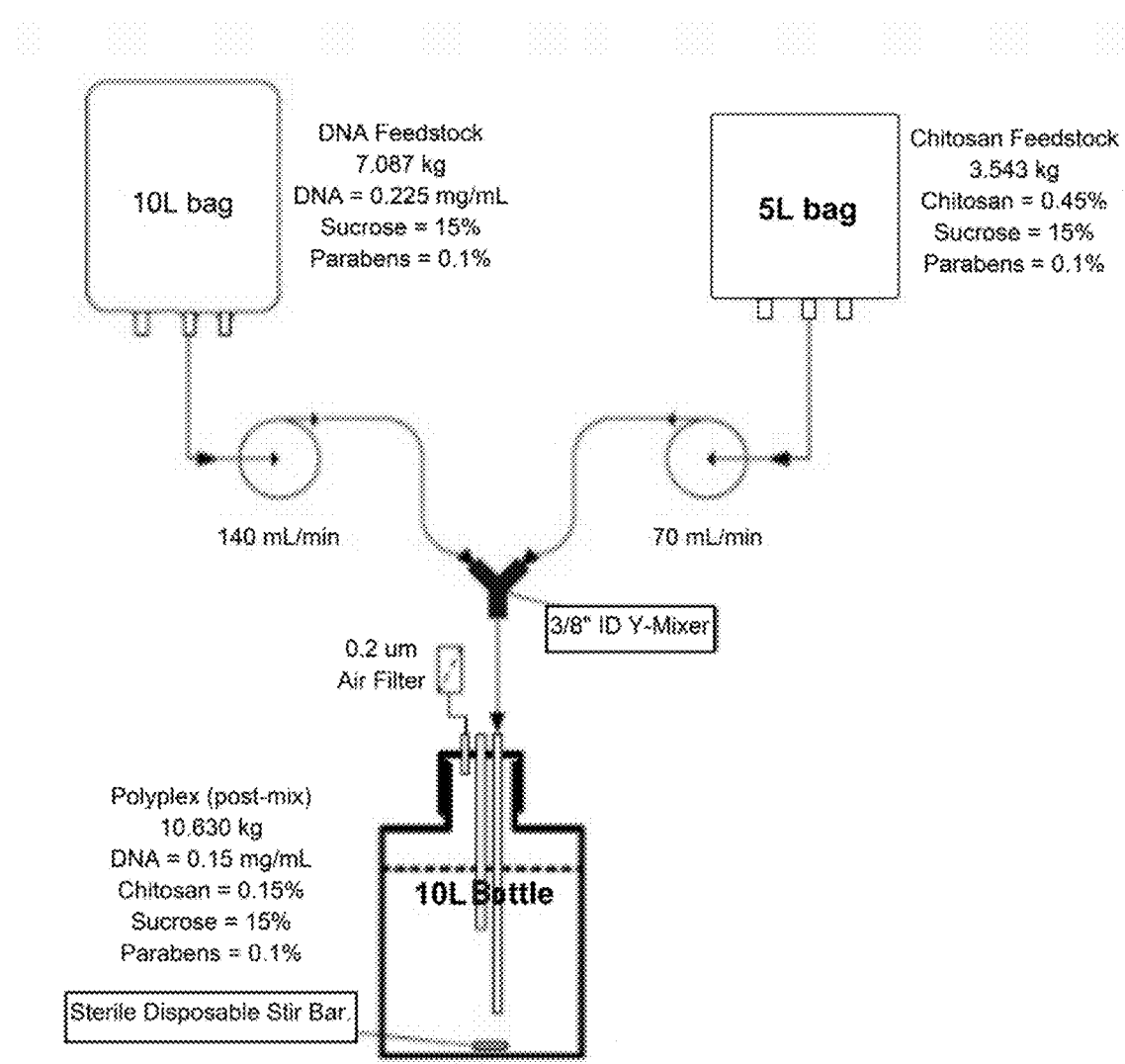
FIG. 3. Schematic drawing of mid-scale in-line mixing process for preparation of 10 L chitosan-nucleic acid polyplex dispersion. All vessels are scaled accordingly for smaller batch sizes. Tubing diameter is 0.48 cm (3/16-inch). Pump flow rates are indicated for a 2:1 DNA:chitosan volume mixing ratio.

A simple mid-scale in-line mixing apparatus was tested using peristaltic pumps, 3/16-inch ID silicone tubing; and a 3/16-inch ID polypropylene junction. A schematic of the set-up with a Y-junction is shown in FIG. 3. Note that the maximum output volume for this set-up limited only by the volume of the feedstock vessels. This process was used to make polyplexes with final DNA concentration of 150 μg/mL at an NP ratio of 20 using 24 mer/98% DDA chitosan. DNA and chitosan feedstocks were mixed at a volume ratio of 2:1 to produce uniform polyplex formulations.

TFF Process

Figure 4:
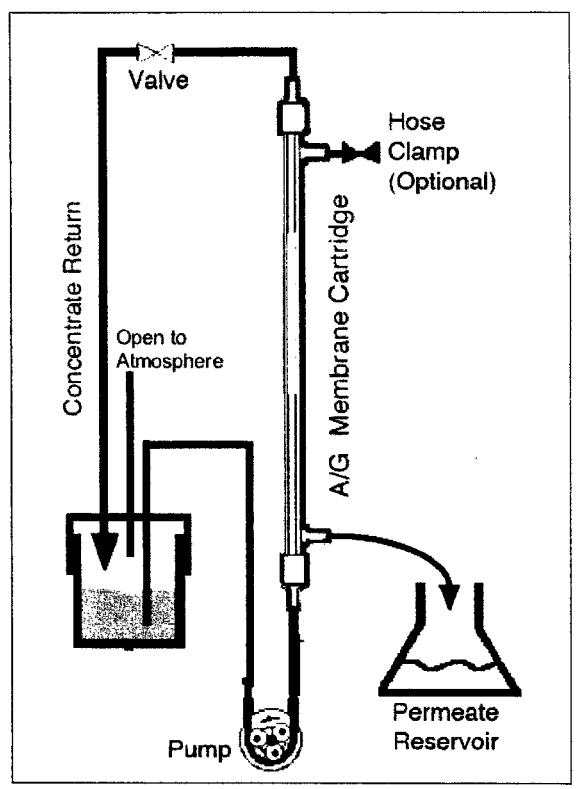
FIG. 4. Schematic drawing of TFF concentration process.

Prior to carrying out TFF studies, the hollow fiber filters were rinsed and cleaned according to the manufacturer's instructions. To carry out concentration, the TFF system was set up as shown in the schematic diagram (FIG. 4) and purged of residual water. After closing the permeate valve and fully opening the backpressure valve, the DNA-chitosan polyplex was added to the product reservoir. Concentration was started by switching on the pump, fully opening the permeate valve and then adjusting the backpressure valve to the target filter inlet pressure. During the concentration process, the mass of permeate collected was monitored on a balance and used to determine when the target DNA concentration had been achieved. See equation below:

$$[DNA]_{Retentate} = [DNA]_{Initial} \times Mass_{Initial} \div (Mass_{Initial} - Mass_{Permeate})$$

After the target volume reduction was attained, the concentration process was stopped by closing the permeate valve and fully opening the backpressure valve. After purging the retentate fluid lines and collecting the final product, a sample of this post-TFF product was submitted for analytical testing and DNA concentration by the picogreen assay. The remainder was stored at 4° C. until completion of analytical testing, and then either promptly used or frozen for storage.

Analytical Testing

Particle Sizing

Particle size measurements were made using a Zetasizer Nano light scattering instrument. In general, samples were either undiluted or diluted 20-fold in 10 mM NaCl (0.4 mL minimum) and loaded into a disposable cuvette. The Zetasizer was programmed to incubate the sample for 3 minutes at 25° C. prior to triplicate 3-minute measurements. Z-average diameter and polydispersity (PDI) were reported with standard deviation (n=3). The Zetasizer was also programmed to account for the composition of the samples with regards to viscosity and refractive index.

Zeta Potential

Zeta potential measurements were made using a Zetasizer Nano light scattering instrument. In general, undiluted samples were loaded into a Zetasizer folded capillary cell (0.8 mL minimum). The Zetasizer was programmed to incubate the sample for 3 minutes at 25° C. prior to replicate measurements (number of replicates were automatically determined by Zetasizer software). Zeta potential values were reported with standard deviation (n=3). The Zetasizer was also programmed to account for the final composition of the samples with regards to viscosity and dielectric constant.

Short-Term Stability by Freezing

For short-term stability studies, final polyplex product was frozen and stored at the appropriate temperature (−20° C., −30° C. or −80° C.). In some cases, samples were rapidly frozen in dry ice/ethanol baths, then stored at the appropriate temperatures. At the appropriate times, samples were thawed to room temperature and analyzed as described.

DNA Quantification with PicoGreen

Prior to DNA measurement using the PicoGreen assay, total DNA must be released from the polyplex by chitosanase. Following release, DNA is subjected to DNA digest with a suitable restriction enzyme to linearize the supercoiled DNA plasmids.

Chitosanase Digestion

To ensure complete release of DNA, polyplex was first diluted to 50 µl in 150 mM NaOAc, pH 5.5 at 37° C. in order to attain a concentration of 0.909-1.818 mM chitosan. (For C(24,98)-N20-c1000 particles, the samples are typically diluted 1/70 and 1/35 to attain the target chitosan concentration.) 50 µl of the diluted polyplex was digested with 50 µl of 4.44 U/mL chitosanase for 2 h at 37° C. (Stock chitosanase concentration is 62 U/mL and was diluted with cold 50 mM NaOAc, pH 5.5 at 37° C.

EcoR1 Digestion

After incubation, *χ µL of the chitosanase-digested sample was added to 5 µL of EcoR1 and 5 µL of EcoR1 buffer and brought to a final 50 µL final volume with MilliQ water. (Sample volume χ µL was adjusted so that final DNA concentration was 4 ng/µL) Typically for C(24,98)-N20-c1000 particle sample, the sample volume χ is 25 µL). The EcoR1 sample was then incubated for 30 min at 37° C.

PicoGreen Assay

The PicoGreen Quant-iT ds DNA HS Assay kit was supplied with two buffers (A and B) and two standards (1 and 2). Buffer A was diluted 1:20 into Buffer B to make solution "A/B". Standards 1 and 2 were diluted 20-fold with solution A/B (10 µL into 200 µL). Final concentrations for standards 1 and 2 were 0 and 10 ng/µL, respectively.

10 to 20 µL of EcoR1 digested sample was brought to a final volume of 200 µL with solution A/B, briefly vortexed, incubated at RT for 2 minutes and then measured for fluorescence on the Qubit Fluorometer according to manufacturer instructions.

Gel Electrophoresis

For verification of DNA capture into the polyplex, samples were subjected to gel electrophoresis. Samples aliquots of 1-5 µL (target of 800 ng DNA) were combined with 2 µL of TrackIt loading buffer and brought to a final 10 µL volume with water. Standard lanes were loaded with Supercoiled DNA ladder. The samples were resolved on a 0.8% agarose gel containing ethidium bromide (50 µg/mL) at 120 V for 45 minutes. The gel was imaged with the FluorChem Imaging System.

In Vitro Transfection

In general, in vitro transfection of 293T-K cells with polyplex formulations was performed in two steps: preparation of cells followed by transfection.

Maintenance of 293T-K Cells

The 293T-K cell line was courtesy of Dr. Kieffer's lab at UBC and were prepared as follows. Human kidney cells were transformed with the SV40 T-antigen; grown in high glucose Dulbecco's Modified Eagle Medium (DMEM) containing 10% fetal bovine serum (FBS) and penicillin/streptomycin; and maintained below 80% confluency.

Preparation of Cells for Transfection

Cells were prepared for transfection as follows. On the day before transfection, 293T-K cells were added to 6-well tissue culture plates ($3 \times 10^5$ cells/well) in 3 mL of complete media (high glucose DMEM+10% FBS+pen/strep). On the day of transfection, cell count was determined for two selected wells by washing cells 1× with phosphate buffered saline (PBS) trypsinizing cells with 1 ml of 0.05% trypsin, adding 1 ml of complete media and counting 10 µl using a hemocytometer. If cells were ~50% confluent (~$7 \times 10^5$ cells/well), then transfection proceeded. (If cells were too sparse or too confluent, then transfection did not proceed.)

Transfection of Cells

Transfection was carried out as follows. First, media was removed from each well followed by addition of 1 mL Opti-mem (adjusted to pH 5.0 with HCl and filtered with 0.2 um filter) to each well, swirling gently and then removal. (Six wells were washed at a time to prevent cells from dislodging.) Then another 1 mL of Opti-mem (pH 5.0) was added carefully to each well so as not to dislodge cells. Next, polyplex samples were added to each well (target of 2 µg DNA), swirled and incubated at 37° C. for 2 h. After incubation, the media was removed and replaced with 2 mL of complete media and re-incubated at 37° C. At the required time points, the supernatant was removed and stored at −20° C. for subsequent SEAP assay.

SEAP Assay

The SEAP assay was performed using the SEAP Chemiluminescent Assay kit. All reagents for the assay were equilibrated at 25° C. for 30 min before use. Standards for the assay were prepared by dissolving placental alkaline phosphatase to 1 mg/mL in 1× dilution buffer from the kit spiked with 0.1% bovine serum albumin and 50% glycerol and then diluting by 10-fold serial dilutions with DMEM to 0.01 pg/uL. Standards and thawed samples were then diluted 1 in 4 with dilution buffer, heat inactivated at 65° C. for 30 min, incubated on ice for 2 min, centrifuged (16100×rcf for 2 min at RT) and the supernatants transferred to new tubes. After equilibrating at 25° C. for 5 min, 50 µL of the samples and standards were added to each well of a Microlite-1 plate in duplicate. Inactivation buffer (50 µL) was then added to each well and pipetted up and down gently to mix, without creating bubbles and incubated for 5 min. The substrate/enhancer reagent was prepared during the 5 min incubation at a ratio for 1:19 of substrate to enhancer. The substrate/enhancer was then added to each well, incubated for 20 min and then the plate was read in the luminometer with an integration time of 1 sec.

Results

Fast Speed in-Line Mixing of C(23,98)-N40-c75+TFF

Polyplex was prepared using the mid-scale inline mixing system at varying flow rates of 90, 210, 270, and 420 mL/min. This mixing system also used an in-line static mixing device in order to assess the utility of the device. This system also did not contain any excipients. In this study, the starting DNA concentration of the polyplex was 0.075 mg/mL and then concentrated by TFF to 0.25 mg/mL.

The flow rates were selected based on the calculated Reynolds number for the in-line static mixing device (Table 2), which determines the minimum number of elements that are required to achieve optimal mixing of a solution at a given flow rate. The equation below is based on the manufacturer's instructions.

$$Re = \frac{3157 \cdot Q \cdot S}{\mu \cdot D}$$

Re = Reynolds number, $Q$ = flow rate (gallons per minute), $S$ = specific gravity, $\mu$ = Viscosity, $D$ = inside tubing diameter

TABLE 2

Calculated Reynolds Number for In-Line Static Mixing Device

| Flow rate (mL/min) | Reynold's Number | Optimal Reynold's Number |
|---|---|---|
| 90 | 311.1 | 500 to 1000 |
| 210 | 694.6 | |
| 270 | 933.2 | |
| 420 | 1451.6 | |

Figure 5:
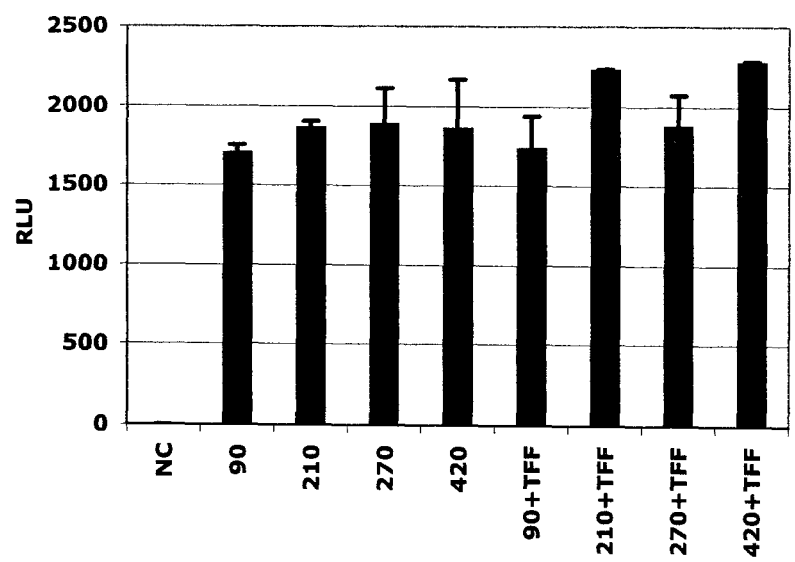
FIG. 5. Graph of in vitro transfection results for polyplex produced by mid-scale process and mixed at different rates.

Table 3 shows that increasing final flow rate of mixing results in an increase in Z-average particle size and PDI. Concentration by TFF showed no significant effect on particle size, PDI, zeta potential, viscosity (Table 3) or in vitro transfection (FIG. 5).

TABLE 3

Size, PDI and Zeta Potential of Mid-Scale Polyplex Mixed at Different Rates

| Flow Rate (mL/min) | | Diameter (nm) | PDI | Zeta Potential (mV) | Viscosity (cp) |
|---|---|---|---|---|---|
| 90 | post-mix | 84.7 ± 1.2 | 0.163 ± 0.013 | 32.4 ± 0.9 | 1.03 |
| " | final | 86.5 ± 0.6 | 0.161 ± 0.004 | 33 ± 1 | 1.06 |
| 210 | post-mix | 87.1 ± 0.7 | 0.170 ± 0.003 | 36 ± 2 | n.d. |
| " | final | 91.4 ± 0.7 | 0.178 ± 0.011 | n.d. | n.d. |
| 270 | post-mix | 91.5 ± 0.7 | 0.199 ± 0.010 | 37 ± 1 | n.d. |
| " | final | 95.9 ± 1.6 | 0.189 ± 0.015 | 36.9 ± 0.5 | 1.07 |
| 420 | post-mix | 98.2 ± 0.4 | 0.214 ± 0.005 | 38 ± 2 | 1.03 |
| " | final | 99.9 ± 1.0 | 0.214 ± 0.009 | 36.2 ± 0.5 | 1.07 |

In-Fine Mixing and TFF Precipitation

In order to achieve DNA concentration of at least 1 mg/mL, we sought to mix polyplex at 0.15 mg/mL DNA then TFF to 1 mg/mL. However, during these studies significant precipitation was observed after the concentration step (data not shown). This occurred at small-scale mixing (3 mL/min and 23 mL/min) and mid scale mixing processes (210 mL/min and 420 mL/min).

Inclusion of Sucrose During Polyplex Formation to Prevent Precipitation

In order to remedy the precipitation problem during TFF, we included all excipients (~10 wt % sucrose, 0.09 wt % methyl paraben, 0.01 wt % propyl parabens) in both the chitosan and DNA feedstocks prior to mixing to form the polyplex. Static mixing device was not used. It was found that the inclusion of the excipients prevented particle aggregation and precipitation during the TFF concentration process. Additionally it was found that the PDI and particle stability were improved when a static mixing device was not included.

Small Scale Batch with Updated Process

A small-scale batch was made using 10% sucrose in the DNA and chitosan feedstocks prior to mixing, and TFF concentration using a recirculation rate of 90 mL/min (shear rate of 7200 $s^{-1}$). After TFF, the particle size were <200 nm with no precipitation. Particle size is summarized in Table 4.

TABLE 4

| TFF fold increase | Diameter (nm) | PDI | [DNA] |
|---|---|---|---|
| mix (pre-TFF) | 100 ± 0.8 | 0.134 | 0.16 |
| 1.5x | 102 ± 1 | 0.150 | 0.23 |
| 3x | 107 ± 0.6 | 0.146 | 0.40 |
| 7.5x | 117 ± 2 | 0.160 | 1.01 |

Figure 6:
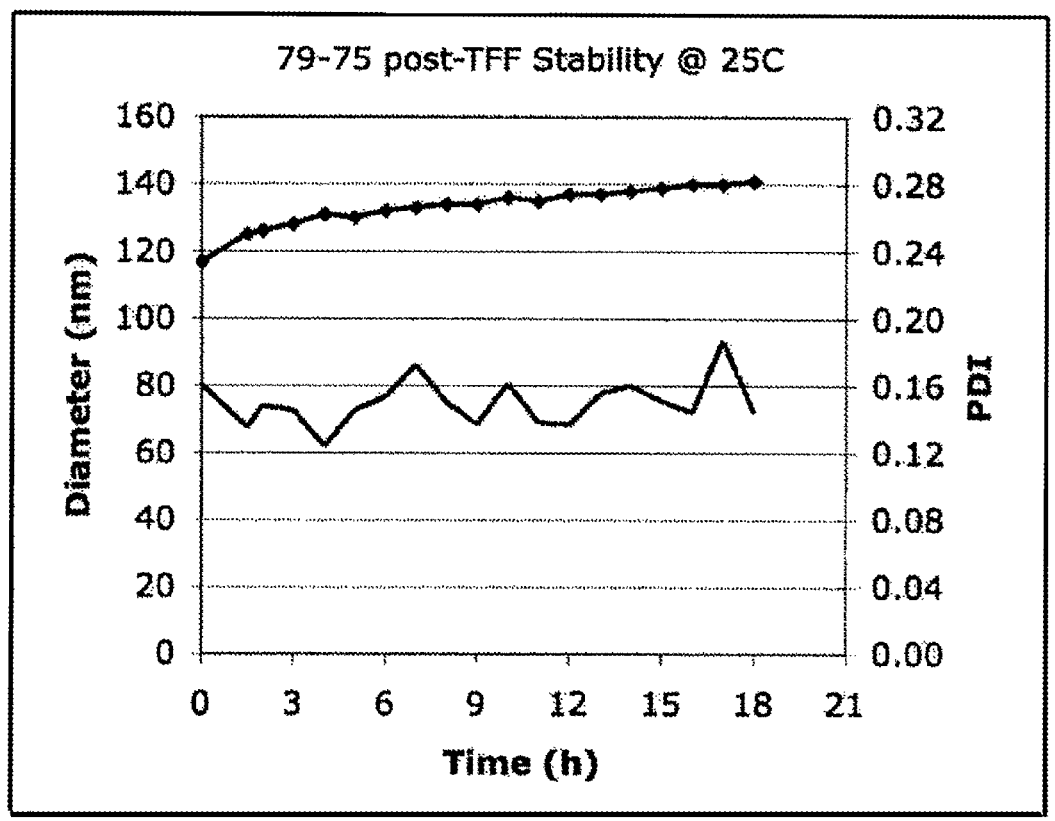
FIG. 6. Graph of stability at room temperature for polyplexes prepared by small-scale mixing with 10% sucrose and fast TFF.

After 18 h at RT, size plateaued to about 140 nm and no precipitation was observed after three days at RT (FIG. 6). In addition, the post-TFF sample had no precipitation after freeze/thaw at either −20° C. or −80° C. After 24 hrs at RT, the thawed particles had plateaued to about 160 and 150 nm for −20° C. and −80° C., respectively (Table 5). In addition, an in vitro transfection assay showed that the batch had biological efficacy (data not shown).

TABLE 5

Small-Scale Mixing with 10% Sucrose and Fast TFF: Freeze-Thaw

| | Freeze-Thaw Condition | | | |
|---|---|---|---|---|
| | −20° C. F/T | −20° C. F/T +24 hrs @ RT | −80° C. F/T | −80° C. F/T +24 hrs @ RT |
| Diameter (nm) | 141 ± 2 | 160 ± 2 | 132 ± 1 | 150 ± 2 |
| PDI | 0.184 | 0.174 | 0.168 | 0.169 |

Mid-Scale Batch with Updated Process

A confirmatory mid-scale batch was made using all of the process changes described above: filtering DNA stock prior to mixing with sucrose solution; including 10% sucrose in the DNA and chitosan feedstocks prior to mixing, and TFF concentration using a recirculation rate of 90 mL/min (shear rate of 7200 s$^{-1}$). In addition, a control batch was made that excluded the sucrose and paraben excipients.

In the non-excipient (control) batch, precipitate was observed readily during and after TFF (data not shown). However, in the excipient batch (Table 6), no precipitate observed until DNA concentration exceeded about 1.5 mg/mL.

TABLE 6

Parameters of Polyplex Batch Including Excipients

| TFF fold increase | Diameter (nm) | PDI | Diameter (nm) +24 hr | PDI +24 hr | [DNA] |
|---|---|---|---|---|---|
| mix (pre-TFF) | | | 96 ± 0.5 | 0.201 | 0.14 |
| 2x | 101 ± 0.5 | 0.207 | 106 ± 0.6 | 0.194 | 0.29 |
| 3.3x | | | 125 ± 0.6 | 0.188 | 0.50 |
| 5x | | | 147 ± 1 | 0.205 | 0.72 |
| 6x | 139 ± 0.6 | 0.193 | 187 ± 2 | 0.210 | 0.90 |
| 8x | 154 ± 0.6 | 0.208 | 232 ± 2 | 0.238 | 0.92 |
| 10x | ppt | | | | |

Mid-Scale 0.8 L Demonstration Batch

We tested the scalability of the in-line mixing process and TFF to a batch size of 0.8 L. Polyplex was mixed to a volume of 0.8 L, and then concentrated to 1.1 mg/mL by TFF. This study included a test of the homogeneity of the mixing process by taking multiple 5 mL aliquots of the mixed polyplex at the beginning, middle and end of the mixing process. The TFF process used a 850 cm$^2$ cartridge (whereas previous small-scale TFF studies used a 73 cm$^2$ cartridge) and incorporated a test of hold times of the concentrated product at 4° C. prior to vialing and freezing at −30° C.

Testing Homogeneity of in-Line Mixing Process

Multiple 0.5 mL samples were collected in the first, middle and final 25 mL of the mixing process to determine homogeneity during the mixing process. The results indicated that the first mixing samples started at around 120 nm, then stabilized to 80 nm after 15 mL of mixing.

TABLE 7

Homogeneity of Mid-Scale In-Line Mixing

| Sample | DNA Concentration (mg/mL) | Z-average diameter (nm) | PDI |
|---|---|---|---|
| Mixing B1 | 0.154 | 118 ± 2 | 0.283 |
| Mixing B3 | N/A | 95 ± 2 | 0.270 |
| Mixing B4 | N/A | 81 ± 2 | 0.186 |
| Mixing B5 | 0.153 | 80 ± 0.7 | 0.189 |
| Mixing M1 | 0.137 | 79 ± 1 | 0.177 |
| Mixing E1 | 0.139 | 83 ± 1 | 0.181 |
| Mixing E3 | 0.136 | 82 ± 1 | 0.183 |

All samples were previously frozen at −30° C., thawed and then analyzed. "B" indicates 5 mL samples from the beginning of the mixing process (first 25 mL) in order from 1 to 5. "M" indicates 5 mL samples from the middle of the mixing process (starting at around 400 mL) in order from 1 to 5. "E" indicates 5 mL samples from the end of the mixing process (starting at around 750 mL) in order from 1 to 5.

Testing Hold Times for Final TFF Product

After the TFF Process was completed, the final TFF product was dispensed into 9×10 mL aliquots (in 20 mL amber glass vials) and sealed. The vials were then subjected to various hold times to mimic typical manufacturing hold conditions:

| (a) 3 vials | Immediately stored @ −30 C. |
|---|---|
| (b) 3 vials | Stored @ 4 C. × 4 h, then stored @ −30 C. |
| (c) 3 vials | Stored @ 4 C. × 24 h, then stored @ −30 C. |

Results of the thawed products indicated good stability of the product over a 24-hour hold time at 4° C. (Table 8). In addition, the post thaw stability over 7 hours for the "4 h@4° C., then −30° C." sample also showed particle stability with an increase of less than 10% compared to the starting material.

TABLE 8

| Sample | DNA Concentration (mg/mL) | Z-average diameter (nm) | PDI |
|---|---|---|---|
| 0 h @ 4° C., then −30° C. | N/A | 110 ± 0.7 | 0.211 |
| 4 h @ 4° C., then −30° C. | 1.139 | 112 ± 0.2 | 0.217 |
| 24 h @ 4° C., then −30° C. | N/A | 114 ± 1 | 0.214 |
| 4 h @ 4° C., then −30° C., then 7 hrs@RT | N/A | 122 ± 0.2 | 0.198 |

All samples were previously frozen at −30° C., thawed and then analyzed.

Mid-Scale 2 L Engineering Run

We tested the scalability of the in-line mixing process and TFF to a batch size of 2 L. Polyplex was mixed to a volume of 2 L, and then concentrated to 1.1 mg/mL by TFF. This study included a repeat test of the homogeneity of the mixing process by taking multiple 5 mL aliquots of the mixed polyplex at the beginning (25 mL discard), middle and end of the mixing process. The TFF process used a 850 cm$^2$ cartridge and incorporated an overnight hold of the final concentrated product at 4° C. prior to vialing and freezing at −30° C.

In general, the physical properties of the polyplexes were well within expected ranges and limits (Table 9).

TABLE 9

| Sample | Z-Avg Diam. (nm) | PDI | Zeta Potential (mV) | Conductivity (mS/cm) |
|---|---|---|---|---|
| Pre-TFF (fresh) | 83 ± 0.5 | 0.167 | N/A | N/A |
| Post-TFF (fresh) | 118 ± 0.6 | 0.207 | +38 ± 3 | 0.525 ± 0.007 |
| Post-TFF (thawed) | 137 ± 0.5 | 0.217 | +34 ± 2 | 0.527 ± 0.008 |

All samples were fresh or previously frozen at −30° C. (as indicated), thawed and then analyzed.

Scalability of in-Line Mixing with Excipients

The following is a summary of physical properties of polyplex batches made by in-line mixing at two different scales and four batch volumes (Table 10). All batches were C(24,98)-N20-c150-pH4.8-Suc15%-Pbn0.1%. Mixing ratios were 2:1 DNA:chitosan. Total flows for small- and mid-scale mixing were 23.3 mL/min and 210 mL/min, respectively. (At these speeds, the linear flow rates through tubing for the two mixing scales was equivalent.)

TABLE 10

Physical Properties of Scaled Mixing Batches

| Batch Size (L) | Mixing Scale | Z-Avg Diam. (nm) | PDI |
|---|---|---|---|
| 0.05 | Small | 95 ± 1 | 0.161 |
| 0.2 | Mid- | 95 ± 1 | 0.183 |
| 0.8 | Mid- | 80 ± 1 | 0.179 |
| 2.0 | Mid- | 83 ± 1 | 0.167 |
| % relative standard deviation | | 9% | 6% |

Testing of DNA Capture by Gel Electrophoresis

Several polyplex formulations were tested for the presence of free DNA to determine if all DNA was captured by chitosan. Overall, no free DNA was observed in any tested formulation (not shown).

In-Vitro Transfection of Polyplexes

In-vitro transfection was carried out on two formulations to compare polyplex made by the drip method (e.g., U.S. Ser. No. 11/694,852) versus in-line mixing. Average transfection efficiency of the in-line mixing method was about 11% greater than the drip method.

| Mixing Method | Average Transfection Efficiency (ng SEAP/mL) |
|---|---|
| Drip | 2810 + 16 |
| In-Line Mixing | 3112 + 150 |

Final polyplex formulations were C(23,98)-N40-Ac10.5-pH4.8-c75. For the in-line mixing batch, the volume mixing ratio of DNA:chitosan was 2:1 and output flow rate was 3 mL/min.

Varying Feedstock Volume Ratios Alters Polyplex Size and PDI

Compositions were prepared according to table 11 using methods described herein.

TABLE 11

| Volume Ratio | DNA working solution concentration (μg/mL) | Chitosan working solution concentration (μg/mL) |
|---|---|---|
| 1:5 | 450 | 1800 |
| 1:2 | 225 | 2250 |
| 1:1 | 150 | 3000 |
| 2:1 | 112.5 | 4500 |
| 5:1 | 90 | 9000 | final target concentrations of 75 μg/mL DNA and 150 μg/mL chitosan

Figure 7:
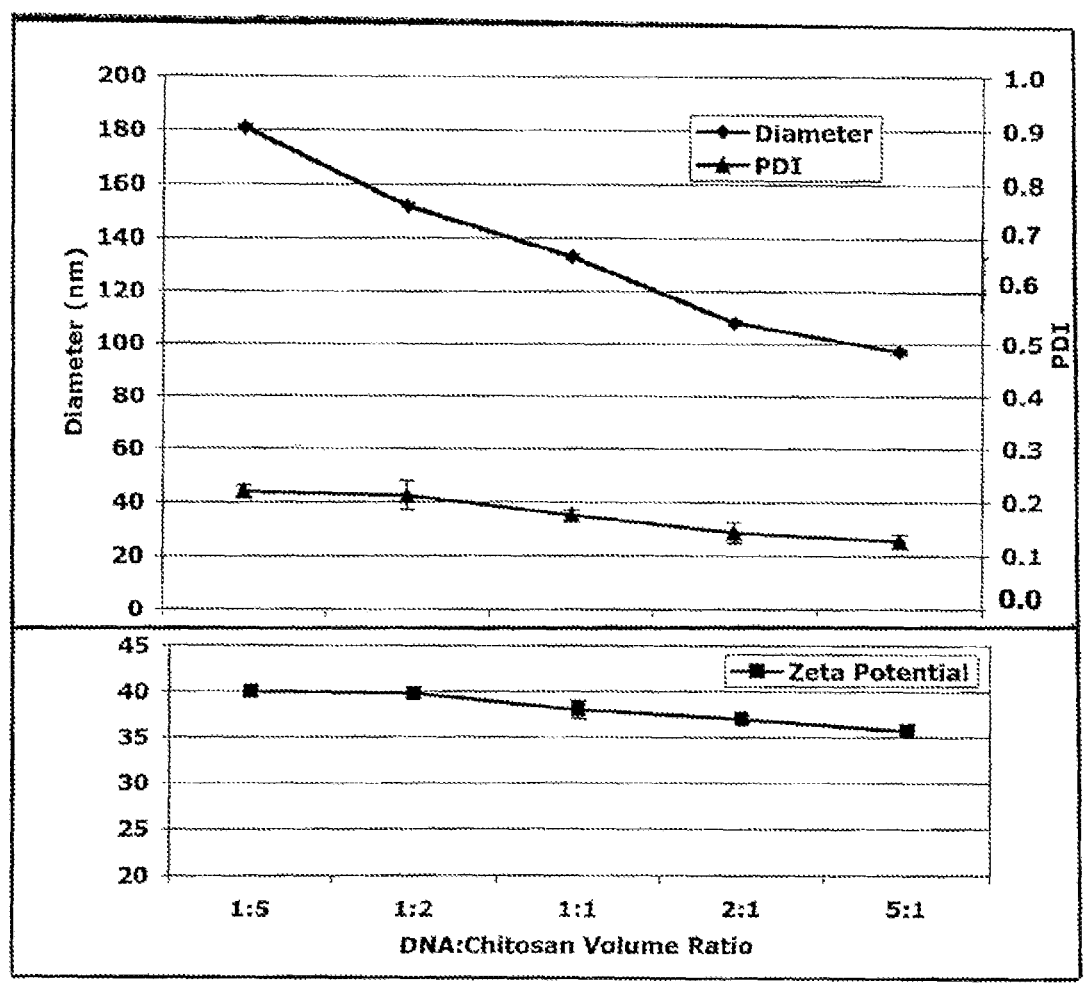
FIG. 7. Graph showing effects of altering volume of feedstocks of DNA and chitosan on polyplex diameter and PDI. Controlling the volume ratio controls particle size. Compositions are described in table 10. All final products were N40-c75.

Particle size and PDI of the preparations were analyzed as described herein. The results are shown in FIG. 7 and establish that particle size can be controlled by altering feedstock volumes while substantially maintaining mixing ratio of chitosan and DNA, and substantially maintaining the mixing concentrations of chitosan and DNA.

All citations are expressly incorporated herein in their entirety by reference.

The invention claimed is:

1. An isotonic composition comprising hydrated chitosan-nucleic acid polyplexes comprising chitosan molecules having an average molecular weight less than 250 kDa and an aggregation inhibitor having a concentration of between about 3% and 20% by weight selected from the group consisting of sucrose, trehalose, glycerol, fructose, and glucose, wherein said composition has a nucleic acid concentration greater than or equal to 0.5 mg/ml and less than or equal to about 1.5 mg/ml and is free of chitosan-nucleic acid polyplex precipitate, and wherein said chitosan-nucleic acid polyplexes have an N:P ratio greater than or equal to 2:1, and increase in average diameter by less than 100% at room temperature in 6 hours.

2. The composition according to claim 1, comprising a nucleic acid concentration greater than 0.75 mg/ml.

3. The composition according to claim 1, comprising a nucleic acid concentration greater than 1.0 mg/ml.

4. The composition according to claim 1, comprising a nucleic acid concentration greater than 1.2 mg/ml.

5. The composition according to claim 1, wherein said polyplexes have an average diameter less than 750 nm.

6. The composition according to claim 1, wherein said aggregation inhibitor is sucrose.

7. The composition according to claim 1, comprising a counter anion concentration less than about 80 mM.

8. The composition according to claim 1, wherein said polyplexes have an average diameter less than 250 nm.

9. The composition according to claim 1, wherein said polyplexes have an N:P ratio greater than or equal to 5:1.

10. The composition according to claim 1, wherein said polyplexes comprise chitosan molecules having less than 3000 glucosamine monomer units.

11. The composition according to claim 1, consisting essentially of said hydrated chitosan-nucleic acid polyplexes and an aggregation inhibitor.

12. The composition according to claim 1, wherein said chitosan-nucleic acid polyplexes have an average polydispersity index of less than 0.5.

13. The composition according to claim 1, wherein said composition is isotonic.

14. An isotonic pharmaceutical composition, comprising hydrated chitosan-nucleic acid polyplexes comprising chitosan molecules having an average molecular weight less than 250 kDa and an aggregation inhibitor having a concentration of between about 3% and 20% by weight selected from the group consisting of sucrose, trehalose, glycerol, fructose, and glucose wherein said composition has a nucleic acid concentration greater than or equal to 0.5 mg/ml and less than or equal to about 1.5 mg/ml and is free of chitosan-nucleic acid polyplex precipitate, wherein said chitosan-nucleic acid polyplexes comprise a therapeutic nucleic acid construct, and wherein said chitosan-nucleic acid polyplexes have an N:P ratio greater than or equal to 2:1, and increase in average diameter by less than 100% at room temperature in 6 hours.

15. The pharmaceutical composition according to claim 14, wherein said aggregation inhibitor is sucrose.

16. The composition according to claim 1 or 14, wherein said chitosan molecules have an average molecular weight less than 100 kDa.

17. The composition according to claim 16, wherein said chitosan molecules have an average molecular weight less than 50 kDa.

18. The composition according to claim 17, wherein said chitosan molecules have an average molecular weight less than 25 kDa.

19. The pharmaceutical composition according to claim 14, wherein said chitosan-nucleic acid polyplexes have an average polydispersity index of less than 0.5.

20. The pharmaceutical composition according to claim 14, wherein said polyplexes have an average diameter less than 200 nm and average polydispersity index of less than 0.3, and said chitosan molecules have an average molecular weight less than 100 kDa.

* * * * *